(12) United States Patent
Inoue (10) Patent No.: US 11,510,552 B2
(45) Date of Patent: Nov. 29, 2022

(54) MEDICAL SYSTEM AND OPERATION METHOD THEREFOR

(71) Applicant: OLYMPUS CORPORATION, Tokyo (JP)

(72) Inventor: Shintaro Inoue, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 276 days.

(21) Appl. No.: 16/711,866

(22) Filed: Dec. 12, 2019

(65) Prior Publication Data

US 2020/0113419 A1    Apr. 16, 2020

Related U.S. Application Data

(63) Continuation of application No. PCT/JP2017/023156, filed on Jun. 23, 2017.

(51) Int. Cl.
*A61B 34/20* (2016.01)
*A61B 1/00* (2006.01)
(Continued)

(52) U.S. Cl.
CPC ........ *A61B 1/00087* (2013.01); *A61B 1/0002* (2013.01); *A61B 1/0005* (2013.01);
(Continued)

(58) Field of Classification Search
CPC ............ A61B 1/00087; A61B 1/00006; A61B 1/0002; A61B 1/0005; A61B 1/00133;
(Continued)

(56) References Cited

U.S. PATENT DOCUMENTS 5,347,987 A * 9/1994 Feldstein ........... A61B 1/00147
600/109
5,836,869 A    11/1998 Kudo et al.
(Continued)

FOREIGN PATENT DOCUMENTS

EP    1 854 420 A1    11/2007
JP    08-164148 A    6/1996
(Continued)

OTHER PUBLICATIONS

International Search Report dated Aug. 22, 2017 received in PCT/JP2017/023156.

*Primary Examiner* — Alexandra L Newton
*Assistant Examiner* — Shankar Raj Ghimire
(74) *Attorney, Agent, or Firm* — Scully, Scott, Murphy & Presser, P.C.

(57) ABSTRACT

A medical system includes: an endoscope and at least one treatment tool; a treatment-tool coordinate calculating unit that extracts the treatment tool by processing two or more images acquired at different times by the endoscope, that determines directions of longitudinal axes of the extracted treatment tool, and that calculates a coordinate of an intersection of the determined two or more longitudinal axes; and a judgment unit that judges whether the treatment tool serves as a follow target, on the basis of the coordinate of the intersection calculated by the treatment-tool coordinate calculating unit.

15 Claims, 7 Drawing Sheets

(51) Int. Cl.
*G06T 7/30* (2017.01)
*G06T 7/00* (2017.01)

(52) U.S. Cl.
CPC ...... *A61B 1/00006* (2013.01); *A61B 1/00133* (2013.01); *G06T 7/0012* (2013.01); *G06T 7/30* (2017.01); *A61B 2034/2065* (2016.02); *G06T 2207/10068* (2013.01); *G06T 2207/30004* (2013.01); *G06T 2210/21* (2013.01); *G06T 2210/41* (2013.01)

(58) Field of Classification Search
CPC .......... A61B 2034/2065; G06T 7/0012; G06T 2207/10068; G06T 2207/30004; G06T 2210/41; G06T 7/246; G06T 2207/30172
See application file for complete search history.

(56) References Cited

U.S. PATENT DOCUMENTS

| | | | |
|---|---|---|---|
| 6,036,637 A | 3/2000 | Kudo | |
| 7,089,928 B2* | 8/2006 | Besharim | A61M 16/0488 128/200.26 |
| 8,480,568 B2* | 7/2013 | Tanaka | A61B 5/416 600/117 |
| 9,469,034 B2* | 10/2016 | Diolaiti | A61B 34/71 |
| 11,179,038 B2* | 11/2021 | Klaiman | A61B 17/12136 |
| 2006/0189842 A1* | 8/2006 | Hoeg | A61B 90/36 600/109 |
| 2007/0055128 A1* | 3/2007 | Glossop | A61B 1/005 600/407 |
| 2007/0265502 A1* | 11/2007 | Minosawa | A61B 1/00177 600/173 |
| 2008/0208041 A1* | 8/2008 | Gilboa | A61B 6/12 600/426 |
| 2008/0287783 A1* | 11/2008 | Anderson | A61B 8/5238 600/429 |
| 2010/0076305 A1* | 3/2010 | Maier-Hein | A61B 6/12 600/426 |
| 2010/0111389 A1* | 5/2010 | Strobel | A61B 6/12 378/62 |
| 2010/0284594 A1* | 11/2010 | Hohne | G06T 19/20 345/419 |
| 2015/0238276 A1* | 8/2015 | Atarot | A61B 1/00009 606/130 |
| 2015/0327940 A1* | 11/2015 | Inoue | A61B 34/37 606/130 |
| 2015/0342442 A1* | 12/2015 | Tadano | A61B 1/00006 600/102 |
| 2016/0000519 A1 | 1/2016 | Dehghan Marvast | |
| 2016/0022125 A1* | 1/2016 | Nicolau | A61B 34/20 600/109 |
| 2016/0104287 A1* | 4/2016 | Ryu | A61B 8/5261 382/131 |
| 2018/0333207 A1* | 11/2018 | Moctezuma De la Barrera | A61B 34/20 |
| 2019/0269461 A1* | 9/2019 | Weingarten | G06T 19/20 |
| 2020/0281660 A1* | 9/2020 | Homan | G06V 40/19 |

FOREIGN PATENT DOCUMENTS

| | | | |
|---|---|---|---|
| JP | H09-38030 A | 2/1997 | |
| JP | H10-314104 A | 12/1998 | |
| JP | 2000-166857 A | 6/2000 | |
| JP | 2003-127076 A | 5/2003 | |
| JP | 2007-159738 A | 6/2007 | |
| JP | 2007-301378 A | 11/2007 | |
| JP | 2016-514531 A | 5/2016 | |
| WO | 2014/155285 A1 | 10/2014 | |
| WO | WO-2015158756 A1 * | 10/2015 | ............ A61B 34/20 |

\* cited by examiner

MEDICAL SYSTEM AND OPERATION METHOD THEREFOR

CROSS-REFERENCE TO RELATED APPLICATIONS

This is a continuation of International Application PCT/JP2017/023156 which is hereby incorporated by reference herein in its entirety.

TECHNICAL FIELD

The present invention relates to a medical system and an operation method therefor.

BACKGROUND ART

There is a known medical system that detects the position of a treatment tool by using a magnetic sensor or a color marker and that moves the field of view of an endoscope so as to follow the treatment tool on the basis of the detected position of the treatment tool (for example, see PTL 1 and PTL 2).

CITATION LIST

Patent Literature

{PTL 1} Japanese Unexamined Patent Application, Publication No. 2000-166857
{PTL 2} Japanese Unexamined Patent Application, Publication No. 2003-127076

SUMMARY OF INVENTION

According to one aspect, the present invention provides a medical system including: an endoscope and at least one treatment tool; a treatment-tool coordinate calculating unit that extracts the treatment tool by processing two or more images acquired at different times by the endoscope, that determines directions of longitudinal axes of the extracted treatment tool, and that calculates a coordinate of an intersection of the determined two or more longitudinal axes; and a judgment unit that judges whether the treatment tool serves as a follow target, on the basis of the coordinate of the intersection calculated by the treatment-tool coordinate calculating unit.

Furthermore, according to another aspect, the present invention provides a medical system including: an endoscope and at least one treatment tool; and a processor configured to process two or more images acquired at different times by the endoscope, wherein the processor is configured to extract the treatment tool by processing the two or more images, determines directions of longitudinal axes of the extracted treatment tool, calculates a coordinate of an intersection of the determined two or more longitudinal axes, and judges whether the treatment tool serves as a follow target, on the basis of the calculated coordinate of the intersection.

Furthermore, according to still another aspect, the present invention provides a medical-system operation method including: acquiring, at different times, two or more images that include at least one treatment tool, by means of an endoscope; extracting the treatment tool from each of the acquired images; determining directions of longitudinal axes of the extracted treatment tool and calculating a coordinate of an intersection of the determined two or more longitudinal axes; and judging whether the treatment tool serves as a follow target, on the basis of the calculated coordinate of the intersection.

DESCRIPTION OF EMBODIMENTS

A medical system 1 and an operation method therefor according to one embodiment of the present invention will be described below with reference to the drawings.

Figure 1:
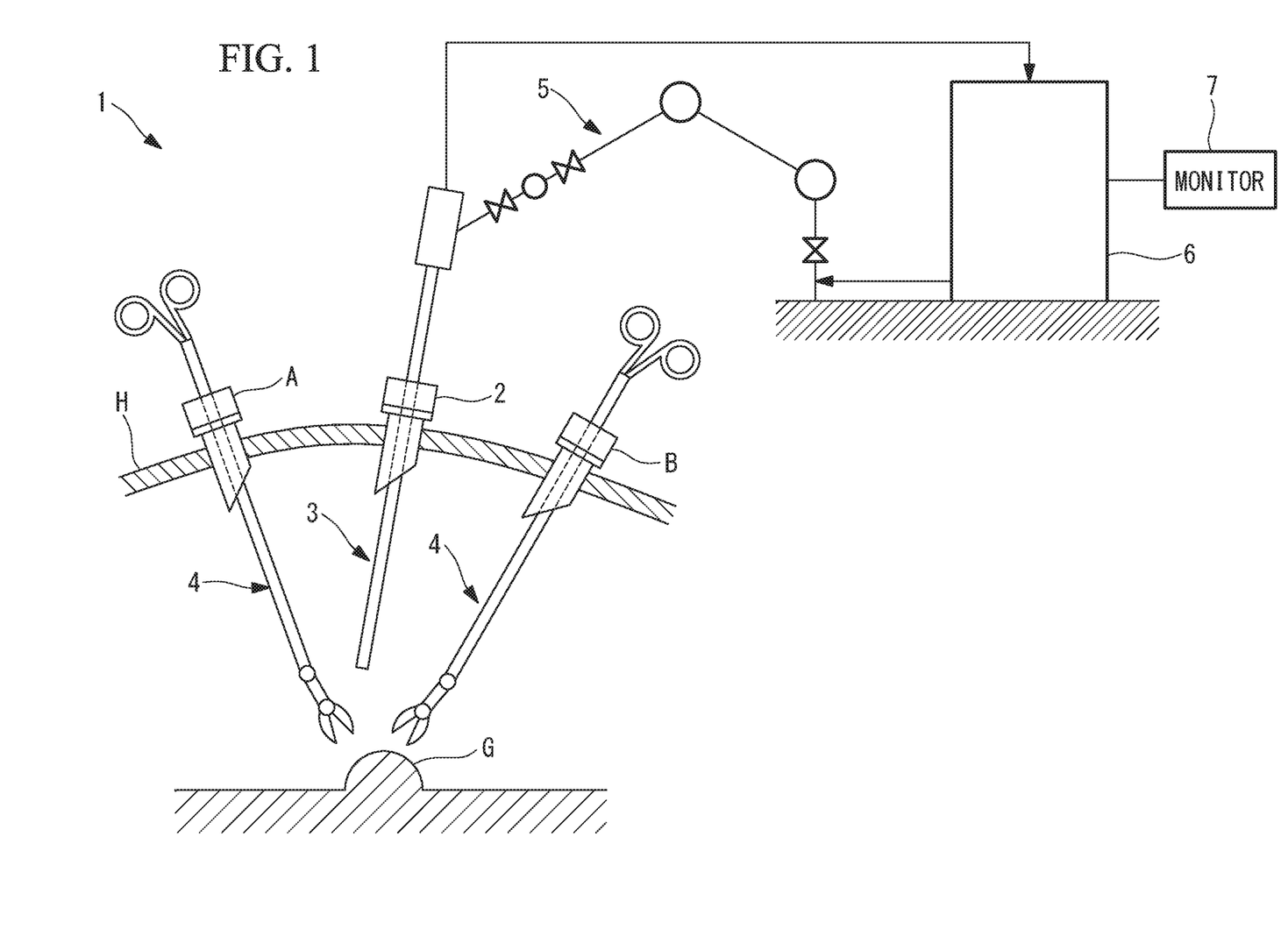
FIG. 1 is a view showing the overall configuration of an example medical system according to one embodiment of the present invention.

As shown in FIG. 1, the medical system 1 of this embodiment includes: an endoscope 3 that is configured such that a distal end thereof is inserted into a body cavity via a trocar 2 disposed while penetrating through a body wall H; one or more, for example, two, treatment tools 4 the distal ends of which are similarly inserted into the body cavity via trocars A and B; a motorized arm (drive mechanism) 5 on which the endoscope 3 is mounted and that moves the position and the orientation of the endoscope 3; a control unit 6 that controls the motorized arm 5 on the basis of an image acquired by the endoscope 3; and a monitor (display unit) 7 that displays the image acquired by the endoscope 3.

The endoscope 3 acquires, in a chronological manner, images each including a treatment-target area (affected area) G in the body cavity and distal-end sections of the treatment tools 4.

The motorized arm 5 is, for example, a 6-axis articulated-type robot, includes a motor (not shown) that drives each axis and an encoder (not shown) that detects a rotation angle of the motor, and is capable of detecting the position and the orientation of the endoscope 3, which is mounted at the distal end of the motorized arm 5, and setting the endoscope 3 at a desired position and in a desired orientation.

Figure 2:
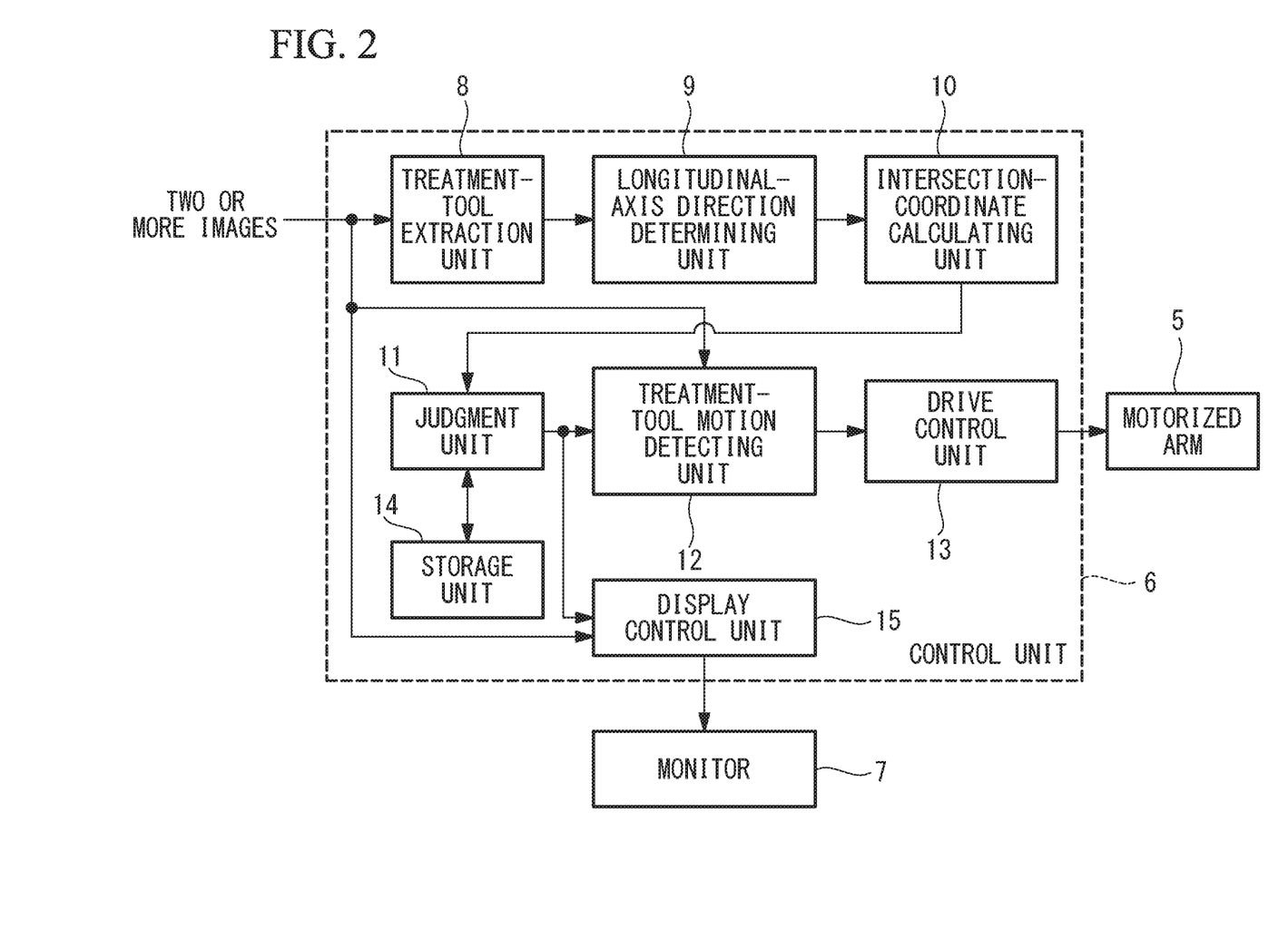
FIG. 2 is a block diagram for explaining a control unit in the medical system shown in FIG. 1.
Figure 3A:
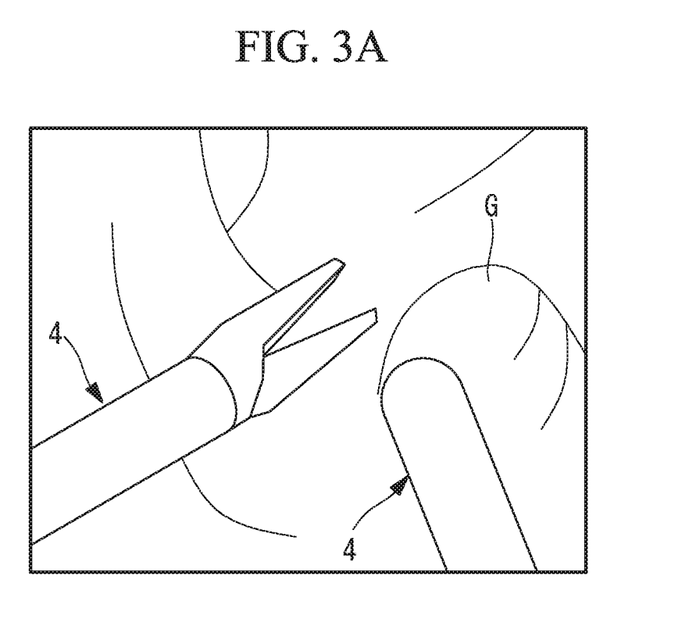
FIG. 3A is a view showing an example endoscopic image acquired by the medical system shown in FIG. 1.
Figure 3B:
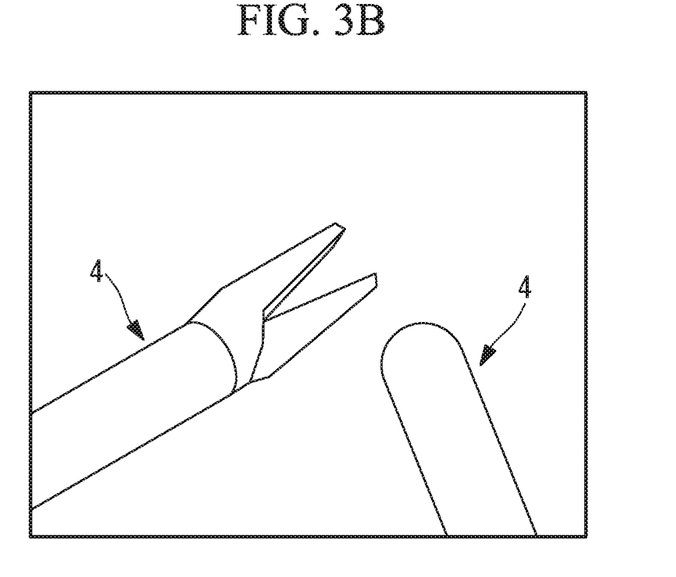
FIG. 3B is a view showing a state in which treatment tools are extracted by processing the image shown in FIG. 3A.
Figure 3C:
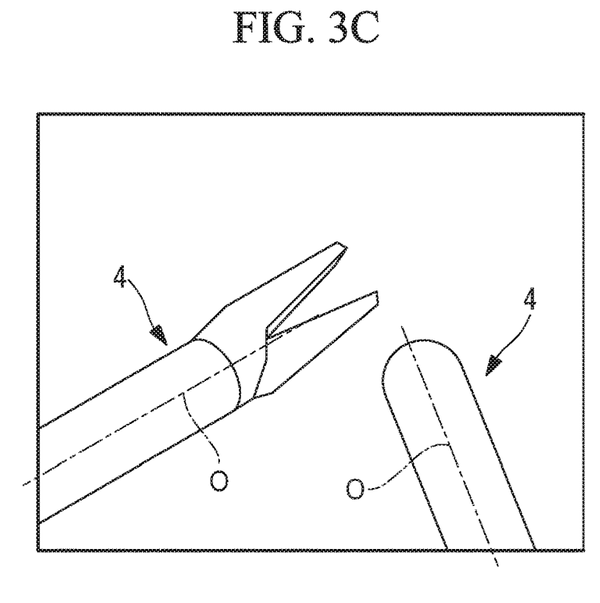
FIG. 3C is a view showing the directions of longitudinal axes of the treatment tools, the longitudinal axes being determined from the outlines of the treatment tools extracted in FIG. 3B.
Figure 3D:
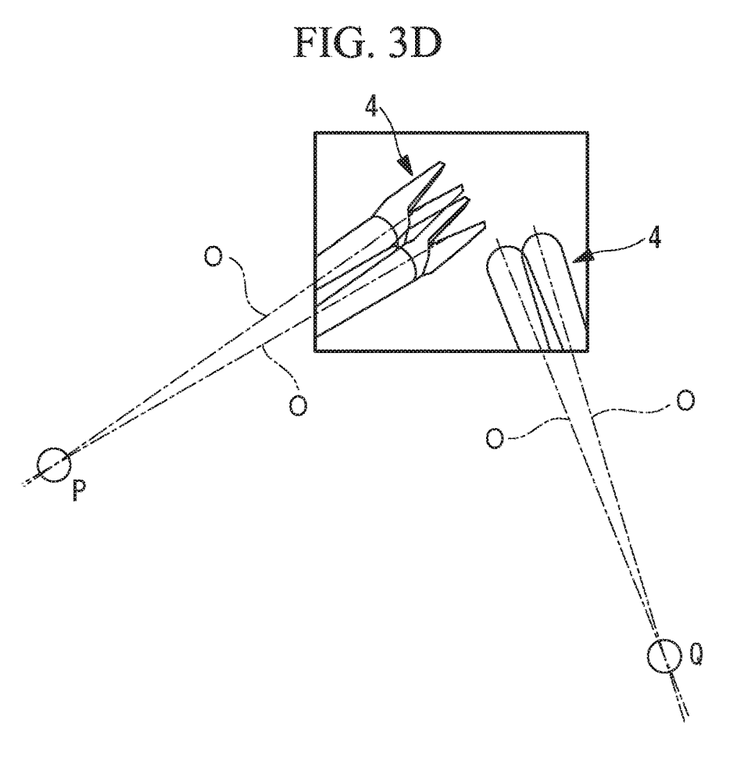
FIG. 3D is a view showing the coordinates of the intersections calculated from the longitudinal axes determined in FIG. 3C.

The control unit 6 is formed of a processor (not shown) and a memory (not shown) and, as shown in FIG. 2, includes: a treatment-tool extraction unit 8 that processes two or more images (see FIG. 3A) acquired at different times by the endoscope 3, to extract the treatment tools 4 from each of the images, as shown in FIG. 3B; a longitudinal-axis direction determining unit 9 that determines the directions of the longitudinal axes O of the extracted treatment tools 4, as shown in FIG. 3C; and an intersection-coordinate calculating unit (treatment-tool coordinate calculating unit) 10 that calculates the coordinates of the intersection P of the longitudinal axes O of one of the treatment tools 4 and the coordinates of the intersection Q of the longitudinal axes O of the other one of the treatment tools 4, the longitudinal axes being determined in the two or more images, as shown in FIG. 3D.

Furthermore, the control unit 6 includes: a judgment unit 11 that judges, on the basis of the coordinates of each of the intersections P and Q calculated by the intersection-coordinate calculating unit 10, whether the treatment tool 4 that has the corresponding longitudinal axes O is a follow target; a treatment-tool motion detecting unit 12 that detects motion of the treatment tool 4 that has been judged as being a follow target; a drive control unit (control unit) 13 that controls the motorized arm 5 so as to cause the field of view of the endoscope 3 to follow the detected motion; and a display control unit 15 that overlays a judgment result on an image acquired by the endoscope 3 and that causes the monitor 7 to display the resulting image.

Furthermore, the control unit 6 includes a storage unit 14 in which the coordinates of a restraint point S of the treatment tool 4 that serves as a follow target are registered in advance.

The treatment-tool extraction unit 8 processes images sent from the endoscope 3 and extracts, as the treatment tools 4, portions having straight edges in the images.

The longitudinal-axis direction determining unit 9 determines, as the longitudinal axes O, the center lines of the treatment tools 4 extracted by the treatment-tool extraction unit 8.

The intersection-coordinate calculating unit 10 overlays the longitudinal axes O of one of the treatment tools 4 determined in the two or more images acquired at different times, thereby calculating the intersection P, which is located on the extensions of these longitudinal axes O.

Figure 4:
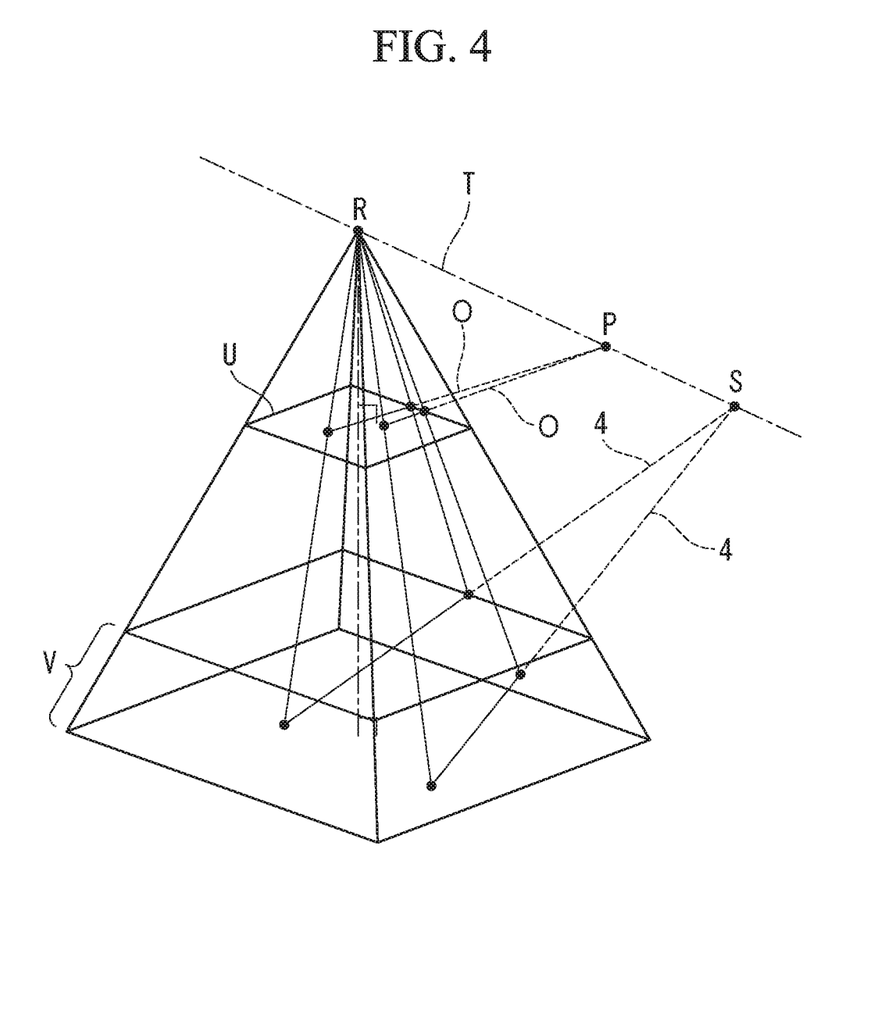
FIG. 4 is a perspective view schematically showing the relationship between the position of the treatment tool and an image, in the medical system shown in FIG. 1.

In the case in which the endoscope 3 acquires two-dimensional images, a principal point R of an optical system provided in the endoscope 3, an imaging surface U, an object V, and the longitudinal axes O of images of the treatment tool 4 projected on the imaging surface U have the positional relationship shown in FIG. 4, and an image of the object V projected on the imaging surface U represents an image acquired by the endoscope 3. FIG. 4 shows, as an example, the positional relationship for the intersection P.

Accordingly, it is conceivable that the restraint point S of the treatment tool 4 exists at any position on a straight line T that connects the intersection P, which is located on the extensions of the longitudinal axes O, and the principal point R of the optical system. Similarly, it is conceivable that the restraint point S of the other treatment tool 4 exists at any position on a straight line T' that connects the intersection Q, which is located on the extensions of the longitudinal axes O, and the principal point R of the optical system.

The judgment unit 11 defines the respective straight lines T and T', which respectively connect the intersections P and Q, which are calculated by the intersection-coordinate calculating unit 10, and the principal point R of the optical system, calculates the distances between the registered restraint point S and the straight lines T and T', and, if any of the distances is equal to or less than a threshold, judges that the treatment tool 4 that has these longitudinal axes O is a follow-target treatment tool 4.

On the other hand, in a case in which the endoscope 3 acquires three-dimensional images, because inclinations of the longitudinal axes O of the treatment tools 4 in the depth direction are also found, it is possible to obtain 3D coordinates as the intersections P and Q of the longitudinal axes O.

In this case, the judgment unit 11 calculates both the distances on the basis of the 3D coordinates of the intersections P and Q, which are calculated by the intersection-coordinate calculating unit 10, and the 3D coordinates of the restraint point S, which are stored in the storage unit 14, and judges whether the treatment tool 4 that has the corresponding longitudinal axes O is a follow-target treatment tool 4.

The treatment-tool motion detecting unit 12 processes the images acquired by the endoscope 3 and detects motion of the treatment tool 4 that has been judged as being a follow-target treatment tool 4 by the judgment unit 11, for example, motion of the position of the distal end of the treatment tool 4.

The drive control unit 13 controls the motorized arm 5 such that the center position of the field of view of the endoscope 3 is disposed so as to conform to the position of the distal end of the treatment tool 4 detected by the treatment-tool motion detecting unit 12. Specifically, the drive control unit 13 drives the motorized arm 5 so as to move the endoscope 3 along a vector from the center position of an image acquired by the endoscope 3 to the position of the distal end of the treatment tool 4 detected in the image.

The operation method for the thus-configured medical system 1 of this embodiment will be described below.

Figure 5:
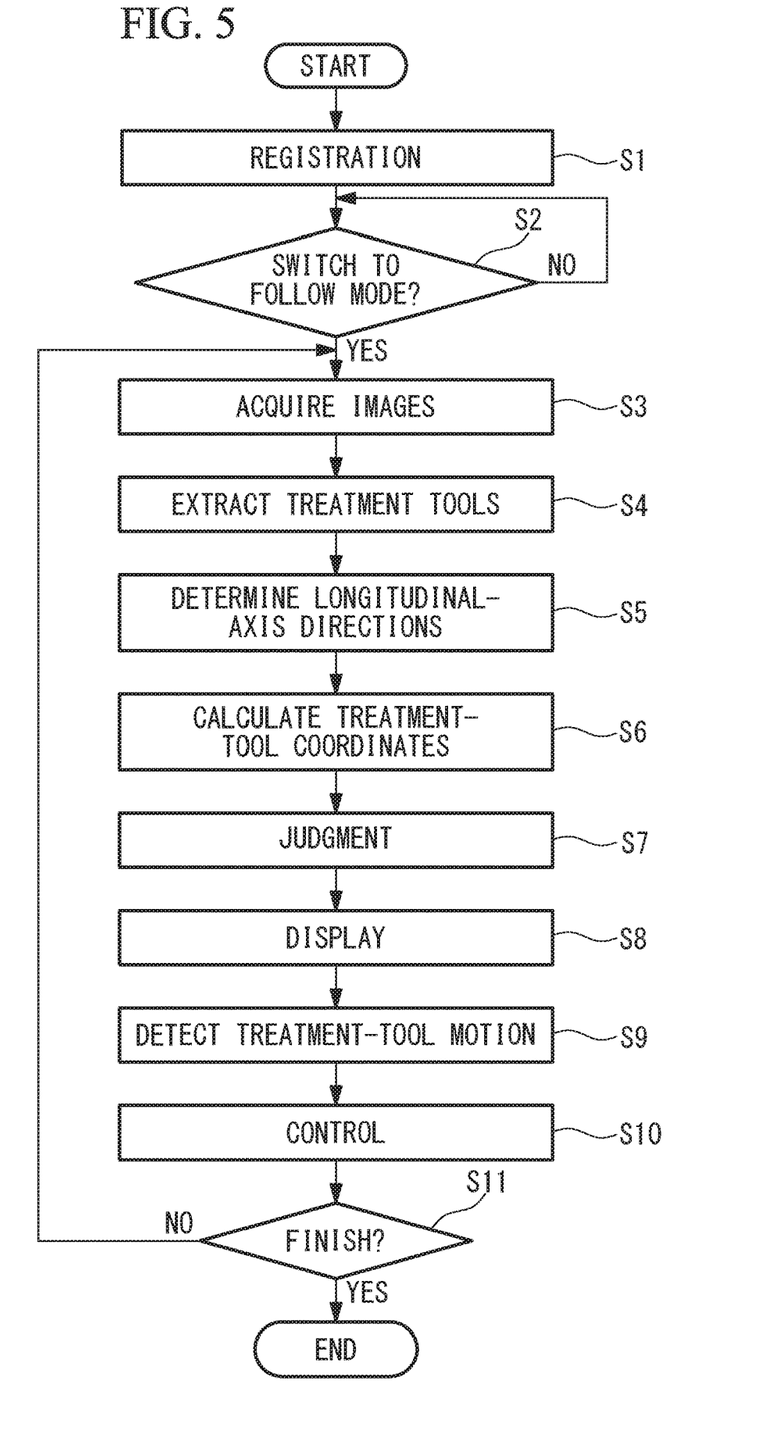
FIG. 5 is a flowchart for explaining an operation method for the medical system shown in FIG. 1.

In order to treat the affected area G in the body cavity by using the medical system 1 of this embodiment, as shown in FIG. 1, the endoscope 3 is inserted into the trocar 2, which is one of the three trocars 2, A, and B disposed while penetrating through the body wall H, the treatment tools 4 are inserted into the other two trocars A and B, and the distal end of the endoscope 3 and the distal ends of the treatment tools 4 are disposed in the body cavity. As shown in FIG. 5, the coordinate position of at least one of the trocars A and B is registered in advance as the trocar (restraint point) A or B into which the treatment tool 4 that serves as a follow target is inserted (registration step S1).

An image of tissue including the affected area G in the body cavity is acquired through actuation of the endoscope 3, the treatment tools 4 are operated such that the two treatment tools 4 are disposed within the image acquired by the endoscope 3, and, in this state, the mode is switched to a follow mode (Step S2). The switching to the follow mode can be performed by means of voice, a foot pedal, or a push button.

In the follow mode, when images at different times are sequentially acquired by the endoscope 3 (image acquisition step S3), the acquired images are sent to the control unit 6 and are subjected to image processing by the treatment-tool extraction unit 8 in the control unit 6, and the treatment tools 4 existing in the images are extracted (treatment-tool extraction step S4).

Next, the longitudinal-axis direction determining unit 9 determines straight lines indicating the directions of the longitudinal axes O, from the outlines of the treatment tools 4 extracted from the images (Step S5).

When the extraction of the treatment tools 4 from the images and the determination of the directions of the longitudinal axes O have been performed on two or more images acquired at different times, because two or more straight lines are determined for each of the treatment tools 4, the coordinates of each of the intersections P and Q of the two or more straight lines are calculated (treatment-tool coordinate calculation step S6).

The calculated coordinates of the intersections P and Q are sent to the judgment unit 11, and the judgment unit 11 calculates the distances between the straight lines T and T', which respectively connect the intersections P and Q and the principal point R of the optical system, and the coordinates of the restraint point S, which are stored in the storage unit 14, and, if any of the distances is equal to or less than the predetermined threshold, judges that the corresponding treatment tool 4 is a follow-target treatment tool 4 (judgment step S7).

Specifically, in a case in which the treatment tool 4 that is inserted into the trocar A, which is one of the two trocars A and B into which the treatment tools 4 are inserted, is always set as a follow-target treatment tool 4, the coordinates of the trocar A are stored as the restraint point S in the registration step S1. Accordingly, merely by checking whether the straight line T or T', which connects the intersection P or Q of the two straight lines detected from the images acquired by the endoscope 3 and the principal point R of the optical system, passes in the vicinity of the restraint point S, it is possible to easily and accurately judge that the treatment tool 4 that has the longitudinal axes O is a follow target.

Because the straight lines indicating the directions of two or more longitudinal axes O determined after extracting the treatment tool 4 that is inserted into the other trocar B form the intersection P or Q on a straight line passing through a position away from the coordinates of the restraint point S by a distance exceeding a predetermined threshold, it is possible to clearly judge that this treatment tool 4 is not a follow target.

Figure 6:
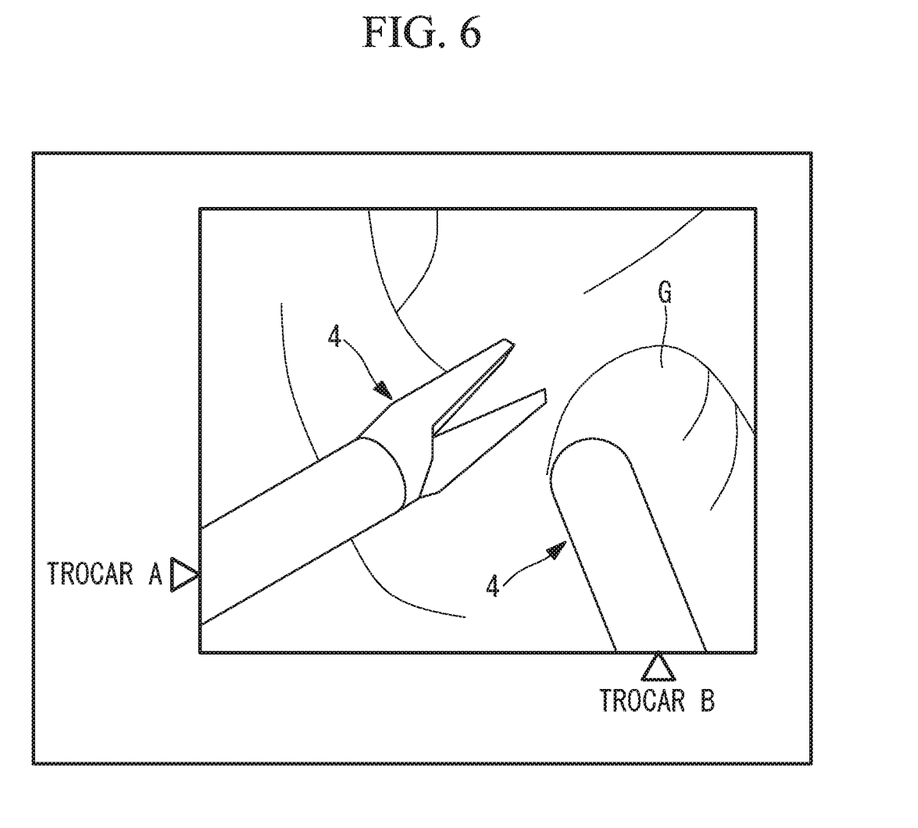
FIG. 6 is a view showing a display example of a judgment result on a monitor, in the medical system shown in FIG. 1.

Then, when the follow target has been judged, as shown in FIG. 6, indications that indicate the positions of the two trocars A and B (for example, characters indicating the trocar A and the trocar B) are displayed, in an overlapping manner, at the positions corresponding to the treatment tools 4 in an endoscopic image displayed on the monitor 7 (display step S8).

Furthermore, at the same time, through processing of the images acquired in a chronological manner, motion of the treatment tool 4 that has been judged as being a follow target is detected by the treatment-tool motion detecting unit 12 (treatment-tool motion detection step S9), and the motorized arm 5 is controlled by the drive control unit 13 (control step S10).

Accordingly, through actuation of the motorized arm 5, the endoscope 3 is made to move so as to follow the motion of the treatment tool 4 that has been judged as being a follow target, and the distal end of this treatment tool 4 is always disposed at the center of the endoscopic image. Specifically, merely by operating the treatment tools 4 while viewing the endoscopic image, an operator can perform treatment on the affected area G, using the treatment tools 4, always at the center of the endoscopic image.

Then, the steps from the image acquisition step S3 are repeated until the end of the follow mode is instructed (Step S11).

Note that, after the endoscope 3 is driven, because the center point of an image acquisition device is displaced, the position of the registered restraint point S needs to be updated from the drive amount of the endoscope 3.

In this way, according to the medical system 1 of this embodiment and the operation method therefor, it is possible to easily and accurately judge, from endoscopic images, whether the treatment tool 4 is a follow target, without mounting a specific magnetic sensor or color marker at the distal end of the treatment tool 4.

Therefore, it is unnecessary to mount a magnetic sensor or a color marker every time the treatment tool 4 serving as a follow target is replaced. Furthermore, even if a plurality of treatment tools 4 of the same type, on which magnetic sensors or color markers are mounted, are inserted, there is an advantage in that any one of the treatment tools 4 can be distinguished, as a follow target, from the other treatment tool(s) 4.

Note that, in this embodiment, although a description has been given of an example case in which the existing endoscope 3 is moved by the motorized arm 5, instead of this, it is also possible to form an electric joint at the distal end of the endoscope 3 and to cause, through actuation of the electric joint, the field of view of the endoscope 3 to follow the motion of the distal end of the treatment tool 4. In this case, in order to detect the position and the orientation of the endoscope 3, the endoscope 3 may be supported by a 6-axis articulated-type support arm capable of detecting the angle of each axis; alternatively, an optical marker or a magnetic marker may be mounted on the endoscope 3, and the position of the optical marker or the magnetic marker may be detected from the outside.

Furthermore, although a description has been given of an example case in which the endoscope 3 is made to follow the follow-target treatment tool 4, instead of this, it is also possible to cause the other treatment tool 4 to follow the follow-target treatment tool 4. For example, when the affected area G is treated by using a second treatment tool 4 while tissue in the vicinity of the affected area G is displaced by using a first treatment tool 4 inserted into the body, there is a case in which it is desired to change the state of displacement using the first treatment tool 4 in accordance with the treatment performed by using the second treatment tool 4.

In such a case, in a state in which the tissue is gripped by the first treatment tool 4, the treatment is performed by using the second treatment tool 4, and the mode is switched to the follow mode, as necessary, by means of voice, a foot pedal, or a push button, thereby moving the first treatment tool 4 so as to follow the second treatment tool 4.

Furthermore, as a method for determining the directions of the longitudinal axes O of the treatment tools 4 in an image acquired by the endoscope 3, as described above, in addition to the method for extracting the treatment tools 4 through image processing, it is also possible to adopt a method for placing markers on the distal end of each of the treatment tools 4 at two or more positions at intervals in the longitudinal direction, a method for extracting the treatment tools 4 by color, or a method in which a learning model for recognizing the treatment tools 4 through AI technology, such as deep learning, is implemented to distinguish the treatment tools 4.

Furthermore, in this embodiment, it is judged whether each of the treatment tools 4 is a follow target on the basis of the corresponding one of the distances between the restraint point S and the straight lines T and T', which connect the principal point R of the optical system and the intersections P and Q of the longitudinal axes O of the treatment tools 4 recognized in images acquired at different times. Instead of this, it is also possible to judge whether each of the treatment tools 4 is a follow target on the basis of the distance between the 2D coordinates of the restraint point S and the 2D coordinates of the intersection P or Q calculated in the images.

Furthermore, in this embodiment, the control unit 6 is hardware formed of a processor and a memory. Instead of this, it is also possible to adopt a configuration in which the memory is connected by a communication line or a configuration in which the control unit 6 is connected to another storage unit by a communication line etc.

The above-described embodiment also leads to the following invention.

According to one aspect, the present invention provides a medical system including: an endoscope and one or more treatment tools; a treatment-tool coordinate calculating unit that extracts the treatment tools by processing two or more images acquired at different times by the endoscope, that determines directions of longitudinal axes of each extracted treatment tool, and that calculates coordinates of an intersection of the determined two or more longitudinal axes; and a judgment unit that judges whether each treatment tool serves as a follow target, on the basis of the coordinates of the intersection calculated by the treatment-tool coordinate calculating unit.

According to this aspect, in a procedure in which the endoscope and the one or more treatment tools are inserted into the body, and treatment is performed by using the treatment tools while a target area is observed by using the endoscope, when two or more images are acquired at different times by the endoscope, the treatment-tool coordinate calculating unit extracts the treatment tools by processing the respective images, determines the directions of longitudinal axes of each treatment tool, and calculates the coordinates of the intersection of the determined two or more longitudinal axes.

Specifically, when the treatment tools included in the images acquired at different times are moved, although the directions of the longitudinal axes of each of the treatment tools change, each treatment tool penetrates through the body wall at the same position if the treatment tool is the same, the longitudinal axes thereof intersect at a single intersection. Therefore, it is possible to specify the position of the body wall through which the treatment tool penetrates, on the basis of the coordinates of the intersection, and to easily distinguish the treatment tool that serves as a follow target, without using a specific magnetic sensor or color marker.

The above-described aspect may further include: a display unit that displays the images acquired by the endoscope; and a display control unit that displays, on the display unit, a judgment result from the judgment unit so as to be associated with the extracted treatment tools, in the images.

By doing so, an operator can easily confirm, on the display unit, whether each treatment tool existing in the image displayed on the display unit is a follow-target treatment tool.

Furthermore, the above-described aspect may further include a storage unit that registers in advance coordinates of a registration point serving as the intersection that can be taken by the treatment tool that serves as the follow target, wherein the judgment unit may judge that the treatment tool that has the longitudinal axes passing through the coordinates of the intersection is the follow target, when a distance between the coordinates of the intersection, which are calculated by the treatment-tool coordinate calculating unit, and the coordinates of the registration point, which are registered in advance in the storage unit, is equal to or less than a predetermined threshold.

By doing so, the registration point serving as the intersection that can be taken by the treatment tool that is a follow target is stored in advance in the storage unit, and, when the coordinates of the intersection of the longitudinal axes of each treatment tool are calculated by the treatment-tool coordinate calculating unit, if the distance between the coordinates of the intersection and the coordinates of the registration point, which is stored in the storage unit, is equal to or less than the predetermined threshold, it is possible to easily judge that the treatment tool is a follow-target treatment tool.

Furthermore, the above-described aspect may further include: a drive mechanism that drives the endoscope or one of the treatment tools; a treatment-tool motion detecting unit that detects motion of the treatment tool that has been judged as being the follow target by the judgment unit; and a control unit that controls the drive mechanism so as to cause the endoscope or the other treatment tool to follow the motion of the treatment tool detected by the treatment-tool motion detecting unit.

By doing so, the treatment-tool motion detecting unit detects motion of the follow-target treatment tool, and the control unit controls the drive mechanism so as to cause the endoscope or the other treatment tool to follow the follow-target treatment tool.

Specifically, when the drive mechanism is provided in the endoscope, it is possible to actuate the drive mechanism so as to move the field of view of the endoscope while following the motion of the treatment tool that has been judged as being a follow target. Furthermore, if the drive mechanism is provided in the other treatment tool, it is possible to cause the other treatment tool to move so as to follow the motion of the treatment tool that has been judged as being a follow target, and to perform treatment, such as displacement of tissue in the vicinity of a target area, through the motion of the follow target.

Furthermore, according to another aspect, the present invention provides a medical system including: an endoscope and one or more treatment tools; and a processor that processes two or more images acquired at different times by the endoscope, wherein the processor extracts the treatment tools by processing the two or more images, determines directions of longitudinal axes of each extracted treatment tool, calculates coordinates of an intersection of the determined two or more longitudinal axes, and judges whether each treatment tool serves as a follow target, on the basis of the calculated coordinates of the intersection.

Furthermore, according to still another aspect, the present invention provides a medical-system operation method including: an image acquisition step of acquiring, at different times, two or more images that include one or more treatment tools, by means of an endoscope; a treatment-tool extraction step of extracting the treatment tools from each of the images acquired in the image acquisition step; a treatment-tool coordinate calculation step of determining directions of longitudinal axes of each treatment tool extracted in the treatment-tool extraction step and of calculating coordinates of an intersection of the determined two or more longitudinal axes; and a judgment step of judging whether each treatment tool serves as a follow target, on the basis of the coordinates of the intersection calculated in the treatment-tool coordinate calculation step.

The above-described aspect may further include a display step of displaying the images acquired by the endoscope and a judgment result obtained in the judgment step, in such a manner as to be associated with the treatment tools extracted from the images in the treatment-tool extraction step.

Furthermore, the above-described aspect may further include a registration step of registering in advance coordinates of a registration point serving as the intersection that can be taken by the treatment tool that serves as the follow target, wherein, in the judgment step, the treatment tool that has the longitudinal axes passing through the coordinates of the intersection may be judged as being the follow target, when a distance between the coordinates of the intersection, which are calculated in the treatment-tool coordinate calculation step, and the coordinates of the registration point, which are registered in advance in the registration step, is equal to or less than a predetermined threshold.

Furthermore, the above-described aspect may further include: a treatment-tool motion detection step of detecting motion of the treatment tool that has been judged as being the follow target in the judgment step; and a control step of controlling a drive mechanism that drives the endoscope or one of the treatment tools, so as to cause the endoscope or the other treatment tool to follow the motion of the treatment tool detected in the treatment-tool motion detection step.

REFERENCE SIGNS LIST 1 medical system
3 endoscope
4 treatment tool
5 motorized arm (drive mechanism)
6 control unit
7 monitor (display unit)
10 intersection-coordinate calculating unit (treatment-tool coordinate calculating unit)
11 judgment unit
12 treatment-tool motion detecting unit
13 drive control unit (control unit)
14 storage unit
15 display control unit
S1 registration step
S3 image acquisition step
S4 treatment-tool extraction step
S6 treatment-tool coordinate calculation step
S7 judgment step
S8 display step
S9 treatment-tool motion detection step
S10 control step
H body wall
O longitudinal axis
P, Q intersection

The invention claimed is:

1. A medical system comprising:
an endoscope; and
a processor configured to:
set a coordinate of a registration point of a treatment tool;
extract the treatment tool from a first image and the treatment tool from a second image, the first image and the second image being acquired at different times by an optical system of the endoscope;
determine a first longitudinal axis of the treatment tool extracted from the first image;
determine a second longitudinal axis of the treatment tool extracted from the second image;
calculate a coordinate of an intersection of the first longitudinal axis and the second longitudinal axis;
calculate a straight line defined by the coordinate of the intersection and a principal point of the optical system;
calculate a distance between the coordinate of the registration point and the straight line; and
determine whether the treatment tool is a follow target based on the distance calculated.

2. The medical system according to claim 1,
wherein the processor is configured to:
control a display to display the first image and the second image; and
control the display to display a result of the determination of whether the treatment tool is the follow target, so as to be associated with the treatment tool extracted from the first image and the treatment tool extracted from the second image.

3. The medical system according to claim 1,
wherein the processor is configured to determine that the treatment tool is the follow target when the distance calculated is equal to or less than a predetermined threshold.

4. The medical system according to claim 1,
wherein the processor is configured to:
control an actuator to drive the endoscope or another treatment tool which is not the follow target;
control a detector to detect motion of the treatment tool determined to be the follow target;
control the actuator so as to cause the endoscope or another treatment tool to follow the motion of the treatment tool determined to be the follow target.

5. The medical system according to claim 1,
wherein the coordinate of the registration point is a first coordinate of a first registration point, the treatment tool is a first treatment tool, the coordinate of the intersection is a first coordinate of a first intersection, the straight line is a first straight line, the distance is a first distance and the follow target is a first follow target, and
wherein the processor is configured to:
set a second coordinate of a second registration point of a second treatment tool;
extract the second treatment tool from the first image and the second treatment tool from the second image;
determine a third longitudinal axis of the second treatment tool extracted from the first image;
determine a fourth longitudinal axis of the second treatment tool extracted from the second image;
calculate a second coordinate of a second intersection of the third longitudinal axis and the fourth longitudinal axis;
calculate a second straight line defined by the second coordinate of the second intersection and the principal point of the optical system;
calculate a second distance between the second coordinate of the second registration point and the second straight line; and
determine whether the second treatment tool is a second follow target based on the second distance calculated.

6. The medical system according to claim 5,
wherein the processor is configured to:
control an actuator to drive the endoscope or the first treatment tool;
control a detector to detect at least one of a motion of the first treatment tool determined to be the first follow target and a motion of the second treatment tool determined to be the second follow target; and
control the actuator to switch between at least two of causing the endoscope to follow the motion of the first treatment tool determined to be the first follow target, causing the endoscope to follow the motion of the second treatment tool determined to be the second follow target and causing the first treatment tool to follow the motion of the second treatment tool determined to be the second follow target.

7. The medical system according to claim 1,
wherein the coordinate of the intersection is disposed outside of the first image and the second image.

8. A medical system comprising:
an endoscope; and
a processor configured to:
   set a coordinate of a registration point of a treatment tool;
   extract the treatment tool from a first image and the treatment tool from a second image, the first image and the second image being acquired at different times by an optical system of the endoscope;
   determine a first longitudinal axis of the treatment tool extracted from the first image;
   determine a second longitudinal axis of the treatment tool extracted from the second image;
   calculate a coordinate of an intersection of the first longitudinal axis and the second longitudinal axis, the coordinate of the intersection being disposed outside of the first image and the second image;
   calculate a distance between the coordinate of the registration point and the coordinate of the intersection; and
   determine whether the treatment tool is a follow target based on the distance calculated.

9. The medical system according to claim 8,
wherein the coordinate of the registration point is a first coordinate of a first registration point, the treatment tool is a first treatment tool, the coordinate of the intersection is a first coordinate of a first intersection, the straight line is a first straight line, the distance is a first distance and the follow target is a first follow target, and
wherein the processor is configured to:
   set a second coordinate of a second registration point of a second treatment tool;
   extract the second treatment tool from the first image and the second treatment tool from the second image;
   determine a third longitudinal axis of the second treatment tool extracted from the first image;
   determine a fourth longitudinal axis of the second treatment tool extracted from the second image;
   calculate a second coordinate of a second intersection of the third longitudinal axis and the fourth longitudinal axis;
   calculate a second straight line defined by the second coordinate of the second intersection and the principal point of the optical system;
   calculate a second distance between the second coordinate of the second registration point and the second straight line; and
   determine whether the second treatment tool is a second follow target based on the second distance calculated.

10. The medical system according to claim 9,
wherein the processor is configured to:
   control an actuator to drive the endoscope or the first treatment tool;
   control a detector to detect at least one of a motion of the first treatment tool determined to be the first follow target and a motion of the second treatment tool determined to be the second follow target; and
   control the actuator to switch between at least two of causing the endoscope to follow the motion of the first treatment tool determined to be the first follow target, causing the endoscope to follow the motion of the second treatment tool determined to be the second follow target and causing the first treatment tool to follow the motion of the second treatment tool determined to be the second follow target.

11. The medical system according to claim 8,
wherein the processor is configured to:
   control a display to display the first image and the second image; and
   control the display to display a result of the determination of whether the treatment tool is the follow target, so as to be associated with the treatment tool extracted from the first image and the treatment tool extracted from the second image.

12. The medical system according to claim 8,
wherein the controller is configured to determine that the treatment tool is the follow target when the distance calculated is equal to or less than a predetermined threshold.

13. The medical system according to claim 8,
wherein the processor is configured to:
   control an actuator to drive the endoscope or another treatment tool which is not the follow target;
   control a detector to detect motion of the treatment tool determined to be the follow target; and
   control the actuator so as to cause the endoscope or another treatment tool to follow the motion of the treatment tool determined to be the follow target.

14. The medical system according to claim 13,
wherein the processor is configured to update the coordinate of the registration point of the treatment tool when the actuator drives the endoscope.

15. The medical system according to claim 8,
wherein the processor is configured to control an actuator to drive the endoscope so as to acquire an image of an end point of the treatment tool.

* * * * *